United States Patent [19]

Guglielmetti

[11] 4,267,343
[45] May 12, 1981

[54] PROCESS FOR THE MANUFACTURE OF 2,5-BIS-(BENZOXAZOLYL)-THIOPHENE COMPOUNDS

[75] Inventor: Leonardo Guglielmetti, Basel, Switzerland

[73] Assignee: Ciba-Geigy Corporation, Ardsley, N.Y.

[21] Appl. No.: 94,150

[22] Filed: Nov. 14, 1979

Related U.S. Application Data

[63] Continuation of Ser. No. 965,719, Dec. 1, 1978, abandoned, which is a continuation of Ser. No. 810,814, Jun. 28, 1977, abandoned.

[30] Foreign Application Priority Data

May 11, 1975 [CH] Switzerland .......................... 5892/77
Jul. 5, 1976 [CH] Switzerland .......................... 8574/76

[51] Int. Cl.³ .................. C07D 409/14; C07D 413/12
[52] U.S. Cl. .................................... 548/220; 548/219; 549/84
[58] Field of Search ........................... 548/220; 549/84

[56] References Cited

U.S. PATENT DOCUMENTS

| | | | |
|---|---|---|---|
| 2,995,564 | 8/1961 | Duennenberger | 260/307 |
| 3,095,421 | 6/1963 | Liechti | 260/304 |
| 3,127,416 | 3/1964 | Liechti | 260/332.2 |
| 3,641,044 | 2/1972 | Matta | 260/307 D |

FOREIGN PATENT DOCUMENTS 940770 11/1963 United Kingdom .

OTHER PUBLICATIONS

Elderfield, "Heterocyclic Compounds", vol. 5, (Wiley & Sons), 1957, p. 438.
Wynberg et al., J. Amer. Chem. Soc. 87,1739–1741, (1965).
Johnson et al., J. Amer. Chem. Soc. 72,514, (1950).
Hinsberg, Berrehtre 43,901–906 (1910) and 45,2413–2418 (1912).
Brown et al., J. Chem. Soc. 1948, 2147.
Johnson et al., Org. Reactions 6, p. 1 (1951).

Primary Examiner—Mark L. Berch
Attorney, Agent, or Firm—John P. Spitals; Edward McC. Roberts

[57] ABSTRACT

A process for the manufacture of 2,5-bis-(benzoxazolyl)-thiophenes of the formula

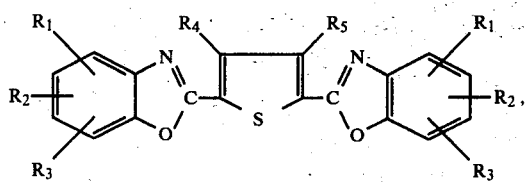

wherein R₁, R₂ and R₃ represent hydrogen or certain non-chromophoric substituents and each of R₄ and R₅ independently represents a hydrogen atom or an alkyl group or together they represent a trimethylene or tetramethylene radical, by reacting a sulphide of the formula

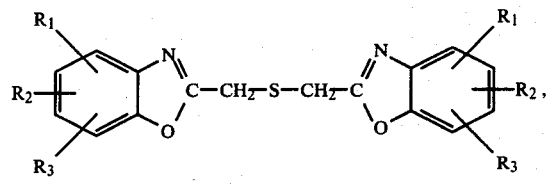

with a dicarbonyl compound of the formula

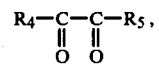

or with a derivative thereof is described.

10 Claims, No Drawings

PROCESS FOR THE MANUFACTURE OF 2,5-BIS-(BENZOXAZOLYL)-THIOPHENE COMPOUNDS

This is a continuation of application Ser. No. 965,719, filed Dec. 1, 1978, now abandoned, which is a continuation of Ser. No. 810,814, filed June 28, 1977, now abandoned.

The present invention provides a process for the manufacture of 2,5-bis-(benzoxazolyl)-thiophene compounds.

Various processes for the manufacture of 2,5-bis-(benzoxazolyl)-thiophene compounds are known from the literature. All these processes start from ortho-aminophenols which are reacted with thiophene derivatives, for example, 2,5-thiophenedicarboxylic acid or 2,5-dicyano-thiophene (cf. U.S. Pat. Nos. 2,995,564, 3,095,421, 3,217,416 and 3,641,044). The manufacture of 2,5-bis-(benzoxazolyl)-thiophenes by condensation of 1,4-bis-(benzoxazolyl)-butanes with sulphur is also known from British patent specification No. 940,770. Compared with these processes, the process of the present invention is characterised by its particular efficiency and economy.

The process according to the invention for the manufacture of 2,5-bis-(benzoxazolyl)-thiophene compounds of the formula

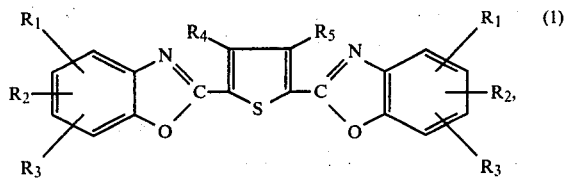

wherein
$R_1$ represents hydrogen, halogen, alkyl of 1 to 18 carbon atoms, haloalkyl, hydroxyalkyl, alkoxyalkyl or cyanoalkyl, each containing 1 to 8 carbon atoms in the alkyl moiety, phenylalkyl containing 1 to 4 carbon atoms in the alkyl moiety whilst the phenyl moiety can be substituted by alkyl groups of 1 to 4 carbon atoms; an alkyl group of 1 to 8 carbon atoms which is substituted by the carboxyl group or a functional derivative thereof, alkenyl of 2 to 4 carbon atoms, cycloalkyl of 5 or 6 carbon atoms, alkoxy of 1 to 6 carbon atoms, phenylalkoxy containing 1 to 4 carbon atoms in the alkoxy moiety, phenoxy, phenyl, each of which can be substituted by halogen, alkoxy or alkyl of 1 to 4 carbon atoms; the carboxy group or a functional derivative thereof, cyano, alkylsulphonyl of 1 to 18 carbon atoms or the sulpho group or a functional derivative thereof, $R_2$ represents hydrogen, alkyl of 1 to 6 carbon atoms, alkoxy of 1 to 4 carbon atoms or halogen, $R_3$ represents hydrogen, chlorine or alkyl of 1 to 4 carbon atoms, and each of $R_4$ and $R_5$ independently represents hydrogen, alkyl of 1 to 10 carbon atoms or together they represent the trimethylene or tetramethylene radical, comprises reacting a sulphide of the formula

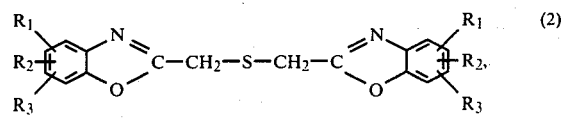

wherein $R_1$, $R_2$ and $R_3$ have the given meanings, with an $\alpha,\beta$-dicarbonyl compound of the formula

wherein $R_4$ and $R_5$ have the indicated meanings, or with a functional derivative of such a compound.

Halogen is to be understood as meaning chlorine, bromine and fluorine, in particular bromine and chlorine, preferably chlorine.

As functional derivatives of carboxyl and sulpho groups there may be mentioned salts, esters and amides. Possible salts are in particular alkali metal, alkaline earth metal, ammonium or amine salts, preferably alkali metal salts.

The reaction according to the invention can be carried out for example at temperatures between $-5°$ and $100°$ C., preferably between $0°$ and $50°$ C. The reaction is also advantageously carried out in the presence of acids or bases, the use of bases being preferred. Suitable bases are inorganic and organic compounds, for example those of lithium, sodium, potassium, rubidium, cesium or ammonium of, for example, the hydroxide, alcoholate or amide types, for example potassium methylate, sodium or potassium ethylate or tertiary amines, such as triethylamine or pyridine. It is preferred to use an alkali metal hydroxide or alkali metal alcoholate as base.

Suitable acids are inorganic and organic acids, for example hydrochloric, sulphuric, glacial acetic, propionic or p-toluenesulphonic acid.

The reaction is advantageously carried out in a solvent which is inert under the reaction conditions. Examples of such solvents are aprotic and protic solvents, preferably water-miscible organic solvents such as methanol, ethanol, isopropanol, butanols, dioxan, dimethyl sulphoxide and dimethyl formamide.

The reaction preferably takes place in anhydrous organic solvents, preferably one in which the base to be used is partially or completely soluble.

The $\alpha,\beta$-dicarbonyl compound of the formula (3) can be used in the free form or in the form of functional derivatives of one or both carbonyl groups. Examples of such derivatives are: acetals (ketals), imines, oximes, hydrazone, and the like. For obtaining compounds of the formula (1), wherein $R_4$ and $R_5$ represent hydrogen, glyoxal or a functional derivative thereof is used as $\alpha,\beta$-dicarbonyl compound of the formula (2). Glyoxal can be used for example in the form of its ordinary commercial aqueous solution, as trimeric glyoxal hydrate or as polymeric glyoxal or also as glyoxal bisulphite, glyoxal sulphate, as acetal or hemiacetal, as mono- or bisaldimine, mono- or bisaldoxime or hydrazone. Preferably an aqueous solution of glyoxal, trimeric and polymeric glyoxal, glyoxal bisulphite and glyoxal bisaldimine is used.

An interesting process within the scope of the present invention is that for the manufacture of 2,5-bis-(benzoxazolyl)-thiophene compounds of the formula

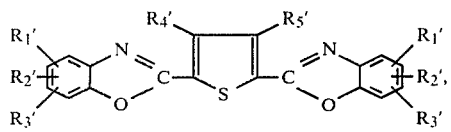

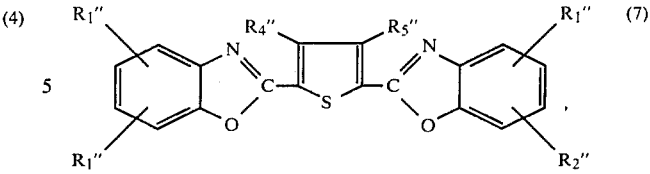

wherein
R₁' represents hydrogen, halogen, alkyl of 1 to 12 carbon atoms, haloalkyl, hydroxyalkyl, cyanoalkyl or phenylalkyl, each containing 1 to 4 carbon atoms in the alkyl moiety, alkyl of 1 to 4 carbon atoms which is substituted by a group of the formula —COOY or —CONY₁Y₂, in which Y represents hydrogen, a salt-forming cation, alkyl of 1 to 18 carbon atoms, alkenyl of 2 to 4 carbon atoms, hydroxyalkyl, cyanoalkyl or phenylalkyl, each containing 1 to 4 carbon atoms in the alkyl moiety, phenyl or phenyl which is substituted by alkyl of 1 to 12 carbon atoms, or alkoxyalkyl of altogether 2 to 8 carbon atoms, and each of Y₁ and Y₂ independently represents hydrogen, alkyl of 1 to 8 carbon atoms, hydroxyalkyl, cyanoalkyl or phenylalkyl, each containing 1 to 4 carbon atoms in the alkyl moiety, or together with the nitrogen atom to which they are attached represent a 5- or 6-membered heterocyclic ring which can additionally contain 1 or 2 further nitrogen and/or oxygen atoms; alkenyl of 3 or 4 carbon atoms, cyclohexyl, alkoxy of 1 to 4 carbon atoms, phenyl, phenoxy, cyano, alkylsulphonyl of 1 to 4 carbon atoms, the sulpho group or an alkali metal salt thereof, or a group of the formula —COOY or CONY₁Y₂ in which Y, Y₁ and Y₂ are as defined above,
R₂' represents hydrogen, alkyl of 1 to 4 carbon atoms, alkoxy of 1 to 4 carbon atoms or chlorine,
R₃' represents hydrogen or methyl, and each of
R₄' and R₅' independently represents hydrogen, alkyl of 1 to 4 carbon atoms, or together they represent the trimethylene or tetramethylene radical,
which process comprises reacting a sulphide of the formula

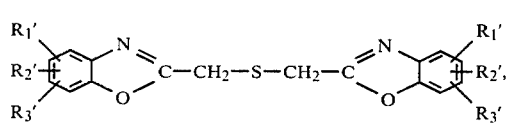

wherein R₁', R₂' and R₃' are as defined above, with a compound of the formula

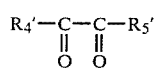

wherein R₄' and R₅' are as defined above, or with a functional derivative thereof.

A preferred process is that for the manufacture of 2,5-bis-(benzaxazolyl)-thiophene compounds of the formula wherein
R₁" represents hydrogen, chlorine, alkyl of 1 to 12 carbon atoms, cyanoalkyl or phenylalkyl, each containing 1 to 4 carbon atoms in the alkyl moiety, carboxyalkyl of 2 to 5 carbon atoms, carbalkoxyalkyl of 3 to 9 carbon atoms, phenyl, cyclohexyl, alkoxy of 1 to 4 carbon atoms, alkylsulphonyl of 1 to 4 carbon atoms, a group of the formula —COOY',
in which Y' represents hydrogen, alkyl of 1 to 18 carbon atoms, alkoxyalkyl of altogether 2 to 6 carbon atoms, phenyl alkyl containing 1 to 4 carbon atoms in the alkyl moiety, alkenyl containing 3 or 4 carbon atoms or an alkali metal or ammonium ion, or a group of the formula —CONY₁'Y₂'
in which Y₁' represents hydrogen, alkyl of 1 to 8 carbon atoms or hydroxyalkyl of 1 to 4 carbon atoms and Y₂' represents hydrogen or alkyl of 1 to 4 carbon atoms,
R₂" represents hydrogen, alkyl of 1 to 4 carbon atoms or alkoxy of 1 to 4 carbon atoms or alkoxy of 1 to 4 carbon atoms, and
each of
R₄" and R₅" represents hydrogen, alkyl of 1 to 4 carbon atoms or together they represent the tetramethylene radical, and those of the formula

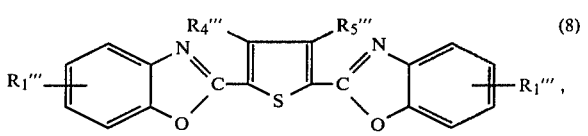

wherein
R₁''' represents hydrogen, alkyl of 1 to 12 carbon atoms, cyclohexyl, carboxyalkyl of 2 to 5 carbon atoms, carbalkoxyalkyl of 3 to 9 carbon atoms, phenylalkyl containing 1 to 4 carbon atoms in the alkyl moiety, phenyl, carboxyl, carbalkoxy of 2 to 5 carbon atoms or alkylsulphonyl of 1 to 4 carbon atoms, and each of R₄''' and R₅''' independently represents hydrogen or alkyl of 1 to 4 carbon atoms,
which process comprises reacting the corresponding sulphides of the formulae

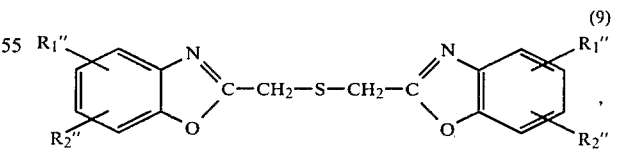

wherein R₁" and R₂" have the given meanings, and

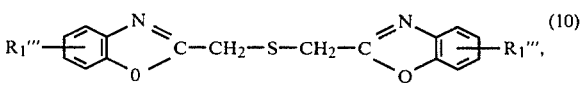

wherein R₁''' has the given meaning, with α,β-dicarbonyl compounds of the formulae

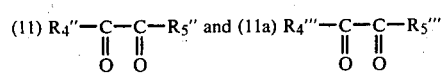

respectively, wherein R₄″, R₅″, R₄‴ and R₅‴ have the given meanings, or with the functional derivatives thereof.

A particularly interesting process is that for the manufacture of 2,5-bis-(benzoxazolyl)-thiophene compounds of the formula

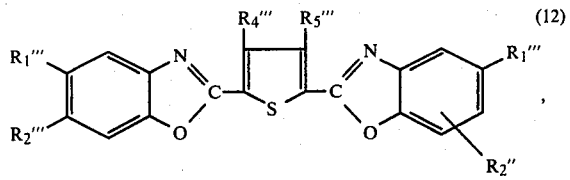

wherein $R_1'''$, $R_4'''$ and $R_5'''$ are as defined in formula (8) and $R_2''$ is as defined in formula (7), which comprises reacting a sulphide of the formula

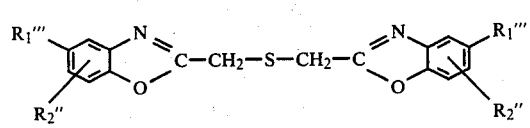

wherein $R_1'''$ and $R_2''$ have the given meanings, with an α,β-dicarbonyl compound of the formula

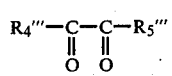

wherein $R_4'''$ and $R_5'''$ have the given meanings, or with a functional derivative thereof.

A particularly preferred process is that for the manufacture of 2,5-bis-(benzoxazolyl)-thiophene compounds of the formula

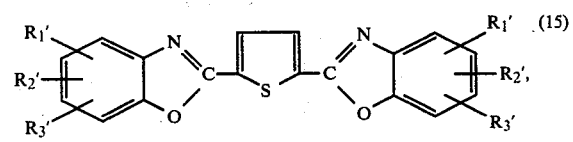

wherein $R_1'$, $R_2'$ and $R_3'$ are as defined in formula (4), and those of the formula

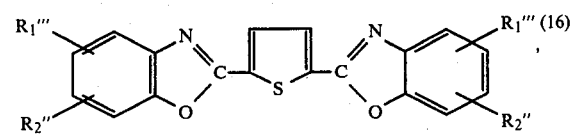

wherein $R_1'''$ is as defined in formula (8) and $R_2''$ is as defined in formula (7), which process comprises reacting a sulphide of the formula

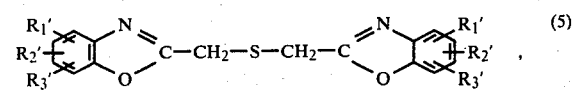

wherein $R_1'$, $R_2'$ and $R_3'$ have the above meanings, or of the formula

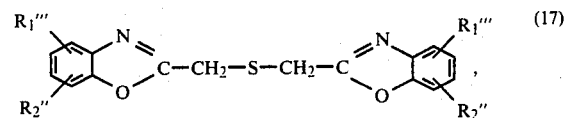

wherein $R_1'''$ and $R_2''$ have the indicated meanings, with glyoxal or with a functional derivative thereof.

A particularly preferred process is that for the manufacture of compounds of the formula

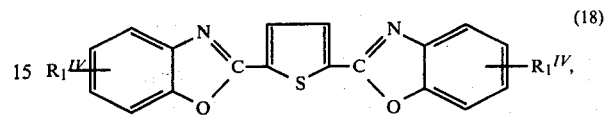

wherein $R_1^{IV}$ represents hydrogen, alkyl of 1 to 4 carbon atoms, chlorine, alkylsulphonyl of 1 to 4 carbon atoms, carboxyl, carbalkoxy of 2 to 5 carbon atoms, benzyl or α,α-dimethylbenzyl, and of the formula

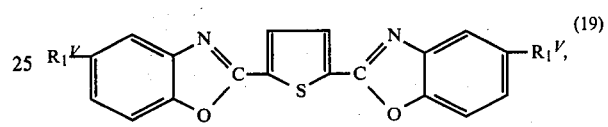

wherein $R_1^V$ represents hydrogen, alkyl of 1 to 4 carbon atoms, benzyl, α,α-dimethylbenzyl or chlorine, which process comprises reacting a sulphide of the formula

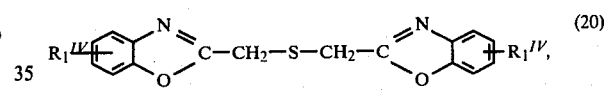

wherein $R_1^{IV}$ has the given meaning, or of the formula

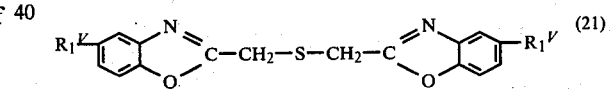

wherein $R_1^V$ has the given meaning, with glyoxal.

The sulphides of the formulae (2), (5), (9), (10), (13), (17), (20) and (21) can be prepared by methods which are known per se.

The sulphides of the formula (2), and thus also the sulphides of the subformulae, can be obtained for example by the following methods:

(a) By condensation of thiodiglycolic acid or thiodiglycolyl dichloride of the formula

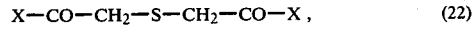

wherein X represents hydroxyl or chlorine, with an o-aminophenol of the formula

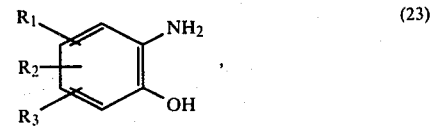

wherein $R_1$, $R_2$ and $R_3$ are as defined in formula (1), (b) By reaction of a 2-chloromethylbenzoxazole of the formula

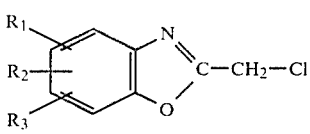

(24)

wherein R₁, R₂ and R₃ have the above meanings, with sodium sulphide.

(c) By reaction of a 2-chloromethylbenzoxazole of the formula (24) with the corresponding 2-mercaptomethylbenzoxazole of the formula

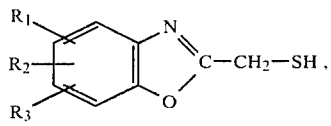

(25)

wherein R₁, R₂ and R₃ have the above meanings.

2-Chloromethyl- and 2-mercaptomethylbenzoxazoles of the formulae (24) and (25) respectively can in turn be obtained for example by condensation either of (1) chloroacetic acid or chloroacetyl chloride or thioglycolic or thioglycolyl chloride with correspondingly substituted o-aminophenols of the formula (23), or (2) the chlorohydrate of 2-chloro- or 2-mercaptoacetimidoalkyl ethers with the correspondingly substituted o-aminophenols of the formula (23).

The compounds of the formulae (1), (4), (7), (8), (12), (15), (16), (18) and (19) are useful fluorescent brighteners for organic materials (cf. U.S. Pat. Nos. 2,995,564, 3,095,421, 3,127,416 and 3,641,044 and also British patent specification 940,770).

In the following Examples the percentages are by weight and melting and boiling points are uncorrected.

EXAMPLE 1

With stirring, 4.6 g of sodium are added in small amounts to 150 ml of anhydrous methanol. The clear sodium methylate solution is cooled to 0° C.

8 g of glyoxal hydrate (trimer) (3C₂H₂O₂.2H₂O), containing 80% of glyoxal to be set free, and 29.6 g of the sulphide of the formula

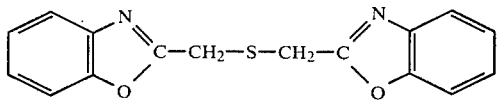

(101)

are dissolved in 150 ml of dimethyl sulphoxide and this solution is added dropwise, with stirring and under nitrogen, in the course of 30 minutes to the above sodium methylate solution which has been cooled to 0° C. The reaction mixture is then stirred for 4 hours at 0° C. under nitrogen, when the reaction product of the formula

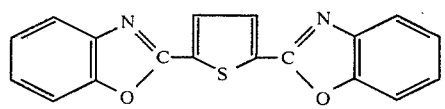

(102)

precipitates in crystalline form. The fairly dense crystalline slurry is subsequently acidified with dilute hydrochloric acid, and filtered by suction. The filter cake is washed neutral and dried in vacuo, affording 28 g (88% of theory) of a slightly yellowish crystalline powder with a melting point of 187° to 207° C. Gas chromatography shows this product to contain 82% of 2,5-bis-[benzoxazolyl(2′)]-thiophene of the formula (102). The product melts at 218°–219° C. after one recrystallisation from chlorobenzene.

The sulphide of the formula (101) used as starting material can be prepared as follows:

54.5 g of o-aminophenol are suspended in 200 ml of chlorobenzene and the suspension is treated with 0.5 ml of pyridine as catalyst. To this reaction mixture is added dropwise, with stirring and under nitrogen, a solution of 59.5 g of chloroacetyl chloride in 100 ml of chlorobenzene in the course of 30 minutes, whereupon the reaction temperature rises to 80° C. The reaction mixture is then heated to 100° C., in the course of which HCl gas evolves and the white suspension passes slowly into solution. The evolution of HCl gas is complete after approx. 2 hours at 100° C. The reaction mixture is then treated with p-toluenesulphonic acid and kept at reflux for 5 hours with stirring and under nitrogen, during which time the water which forms is collected in a steam trap. The clear reaction solution is concentrated to dryness in vacuo, affording 86 g (approx. 100% of theory) of a slightly brownish oil, which gas chromatography shows to have a content of 82.9% of 2-chloromethylbenzoxazole of the formula

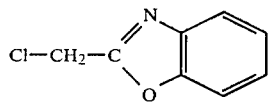

(103)

63 g of sodium sulphide are dissolved in 200 ml of water and the solution is treated with 0.8 g of benzyl-tri-n-butylammonium bromide as phase transfer catalyst. To the vigorously stirred reaction mixture, which has been cooled to 10° C., is added dropwise in the course of 30 minutes a solution of 86 g of the 2-chloromethylbenzoxazole of the formula (103) in 200 ml of methylene chloride. The reaction mixture is thereafter stirring for a further 3 hours at room temperature. The methylene chloride layer is then washed neutral with water, dried over sodium sulphate and freed from methylene chloride in vacuo, affording 70 g (94% of theory) of a slightly brownish crystalline slurry, which gas chromatography shows to have a content of 77.4% of sulphide of the formula (101). The product melts at 75°–76° C. after two recrystallisations from alcohol.

The sulphide of the formula (101) can also be obtained by condensation of 1 mole of thiodiglycolic acid with 2 moles of o-aminobenzene in dichlorobenzene at 150° C. in the presence of p-toluenesulphonic acid as catalyst.

EXAMPLE 2

A methanolic sodium methylate solution (18 g) is diluted with 50 ml of dimethyl formamide and cooled to 0° C. With stirring and under nitrogen, a solution of 8.5 g of glyoxal hydrate (trimer) (3C₂H₂O₂.2H₂O), with an 80% content of glyoxal to be set free, in 50 ml of dimethyl formamide, and a solution of 29.6 g of the sulphide of the formula (101) in 50 ml of dimethyl formamide, are added dropwise separately, but simultaneously, to the above solution at 0° to 5° C. in the course of 30 minutes. The reaction mixture is subsequently stirred for a further 3 hours at 0° to 5° C. under nitrogen, in the course of which the reaction product of the formula (102) precipitates in crystalline form. The fairly dense crystalline slurry is then further stirred for 2 hours at room temperature and for a further 2 hours at 40° to 45° C., then cooled to 0° C., diluted with a mixture of methanol/water (1:1), and filtered by suction. The filter cake is washed neutral firstly with 20 ml of methanol and then with water and dried in vacuo, affording 23.5 ml (74% of theory) of the analytically pure compound of the formula (102) in the form of a pale yellow crystalline powder with a melting point of 218°–219° C.

EXAMPLE 3

11.2 g of potassium hydroxide powder are dissolved in 200 ml of anhydrous methanol and the clear solution is cooled to 0° C.

14 g of glyoxal hydrate (trimer) ($3C_2H_2O_2.2H_2O$), with an 80% content of glyoxal to be set free, and 59.2 g of the sulphide of the formula (101), are dissolved in 200 ml of dimethyl sulphoxide and this solution is added dropwise in the course of 2 hours, with stirring and under nitrogen, to the methanolic potassium hydroxide solution which has been cooled to 0° C. The reaction mixture is further stirred for 20 hours at 0° C. under nitrogen, in the course of which time the reaction product precipitates in crystalline form. The fairly dense crystal slurry is further stirred for 2 hours at 40° C. to 45° C., cooled, diluted with water and filtered by suction. The filter cake is washed neutral firstly with 200 ml of a 1:1 mixture of isopropanol/water and then with water and dried in vacuo, giving 47.5 g (74.5% theory) of the analytically pure compound of the formula (102) in the form of a pale yellow crystalline powder with a melting point of 217° to 218° C.

EXAMPLE 4

19.5 g of sodium acetate (anhydrous) are dissolved hot in 150 ml of glacial acetic acid. The clear solution is cooled to room temperature and then 8.5 g of glyoxal hydrate (trimer) ($3C_2H_2O_2.2H_2O$), with an 80% content of glyoxal to be set free, and 29.6 g of the sulphate of the formula (101), are added. The reaction mixture is heated and thereafter kept for 16 hours at reflux and then freed in vacuo from glacial acetic acid. The residue is taken up in water and extracted with methylene chloride. The methylene chloride extract is washed neutral with water, dried over sodium sulphate and concentrated to dryness in vacuo, giving 21 g (66% of theory) of the compound of the formula (102) in the form of a brownish crystalline powder with a melting point of 175°–200° C. The product melts at 216° C. after two recrystallisations from chlorobenzene.

EXAMPLE 5

29.6 g of the sulphide of the formula (101) are dissolved in 150 ml of glacial acetic acid. To this clear sulphide solution, which is heated to 80° C., are added dropwise in the course of 15 minutes 23.5 g of a 30% aqueous glyoxal solution. The reaction mixture is further stirred for 4 hours at 80° C. and then concentrated to dryness in vacuo. The crystalline residue is taken up in 100 ml of methanol and collected by suction filtration, giving 13 g (41% of theory) of the compound of the formula (102) in the form of a light brown crystalline powder with a melting point of 189°–193° C. The product melts at 218°–219° C. after two recrystallisations from chlorobenzene.

EXAMPLE 6

29.6 g of the sulphide of the formula (101) and 8.5 g of glyoxal hydrate (trimer) ($3C_2H_2O_2.2H_2O$), with an 80% content of glyoxal to be set free, are taken up in 150 ml of acetic anhydride. The white suspension is kept at reflux for 24 hours, then cooled, and the crystalline precipitate of the reaction product, is filtered off by suction. The filter cake is washed with glacial acetic acid and dried in vacuo, affording 10 g (31% of theory) of the compound of the formula (102) in the form of a light brown crystalline powder with a melting point of 212°–215° C. The product melts at 218°–219° C. after one recrystallisation from chlorobenzene.

EXAMPLE 7

29.6 g of the sulphide of the formula (101) and 26 g of N-o-toluidine-glyoxal bisaldimine are taken up in 100 ml of dimethyl formamide. The reaction mixture is heated to 80° C. to give a clear solution. To this solution is then added 1 g of pulverised potassium hydroxide. The reaction mixture is subsequently further stirred for 5 hours at 85° to 90° C., then cooled to 0° C., diluted with water and extracted with chloroform. The chloroform extract is washed neutral with water, dried over sodium sulphate and concentrated to dryness in vacuo, giving 46 g of a strongly fluorescing oil which is chromatographed twice over alumina. Elution with chlorobenzene yields 8.4 g (26.4% of theory) of the compound of the formula (102) as light brown crystals with a melting point of 195°–200° C. The product melts at 218°–219° C. after two recrystallisations from ethyl acetate.

EXAMPLE 8

29.6 g of the sulphide of the formula (101), 16.6 g of N-tert.-butylamine-glyoxal bisaldimine and 100 ml of dimethyl formamide are heated, with stirring, to 140° C. The mixture is further stirred for 4 hours at 140°–145° C., in the course of which tert.-butylamine evolves. The reaction mixture is subsequently cooled to 0° C. and worked up as described in Example 7. Purification by chromatography over alumina yields 9 g (28% of theory) of the compound of the formula (102) in the form of light brown crystals with a melting point of 192° to 200° C. The product melts at 218°–219° C. after two recrystallizations from ethyl acetate.

EXAMPLE 9

4.6 g of sodium are added in small amounts, with stirring, to 200 ml of anhydrous methanol. The clear sodium methylate solution is cooled to 0° C.

8.5 g of glyoxal hydrate (trimer) ($3C_2H_2O_2.2H_2O$), with an 80% content of glyoxal to be set free, and 40.8 g of the sulphide of the formula

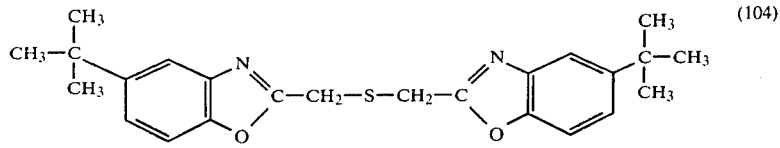

are dissolved in 200 ml of dimethyl sulphoxide and this solution is added dropwise, with stirring and under nitrogen, to the sodium methylate solution which is cooled to 0° C., in the course of 30 minutes. The reaction mixture is then further stirred overnight at 0° C. under nitrogen, when the reaction product of the formula

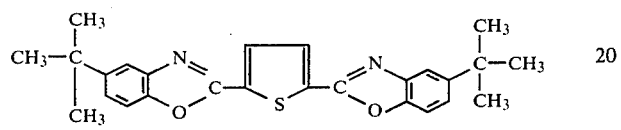

precipitates in partially crystalline form. The reaction mixture is then acidified with dilute hydrochloric acid, freed from methanol in vacuo and filtered by suction. The filter cake is washed neutral with water and dried in vacuo, giving 43 g (100% of theory) of a slightly brownish crystalline powder with a melting point of 150° to 176° C. Gas chromatography shows this product to have a content of 79.4% of 2,5-bis-[5'-tert.-butyl-benzoxazolyl-(2')]-thiophene of the formula (105). The product melts at 200°-201° C. after two recrystallisations from ethyl acetate.

The sulphide of the formula (104) used as starting material can be prepared as follows:

151 g of chloroacetonitrile and 100 ml of anhydrous ethanol are taken up in 1000 ml of anhydrous ether. The solution is cooled to 5° C. and, with stirring, saturated at this temperature with a dry flow of HCl gas, whereupon the reaction product of the formula

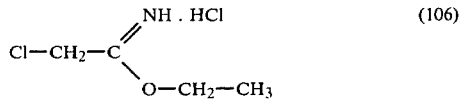

precipitates in crystalline form. The reaction mixture is subsequently allowed to stand for 24 hours at 0° C., then filtered by suction. The filter cake is washed with anhydrous ether, giving 308 g (98% of theory) of the chlorohydrate of the chloroacetimidoethyl ether of the formula (106) in the form of colourless crystals.

324 g of 2-amino-4-tert.-butylphenol are suspended in 2000 ml of chloroform and the suspension is treated in small amounts with 308 g of the above chlorohydrate of the chloroacetimidoethyl ether of the formula (106) at room temperature. The reaction is slightly exothermic. After it has been stirred for 24 hours at room temperature, the reaction mixture is diluted with 1000 ml of water. The organic layer is separated, washed neutral with water, dried over sodium sulphate and freed from chloroform in vacuo, affording 409 g (93% of theory) of a slightly brownish oil which gas chromatography shows to have a 90.5% content of 2-chloromethyl-5-tert.-butyl-benzoxazole of the formula

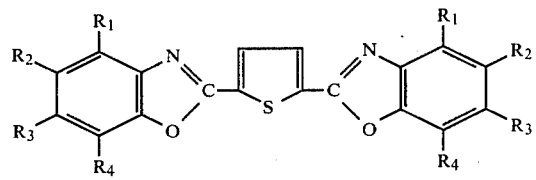

230 g of sodium sulphide are dissolved in 700 ml of water and the solution is treated with 3.5 g of benzyl-tri-n-butylammonium chloride as phase transfer catalyst. To the vigorously stirred reaction mixture, which has been cooled to 0° C., is added dropwise in the course of 30 minutes a solution of 409 g of the above 2-chloromethyl-5-tert.-butyl-benzoxazole of the formula (107) in 700 ml of methylene chloride. The reaction mixture is subsequently further stirred for 24 hours at room temperature. The methylene chloride layer is then washed neutral with water, dried over sodium sulphate and freed from methylene chloride in vacuo, affording 370 g (99% of theory) of a slightly brownish crystalline slurry, which gas chromatography shows to have an 86% content of sulphide of the formula (104). The product melts at 92°-93° C. after two recrystallisations from ethanol.

The compounds of the formula listed in Table I are obtained in a manner analogous to that described for obtaining the compound of the formula (105).

TABLE I

| Compound No. | $R_1$ | $R_2$ | $R_3$ | $R_4$ | Melting point °C. |
|---|---|---|---|---|---|
| 108 | —H | —Cl | —H | —H | 297–299 |
| 109 | —CH₃ | —H | —H | —H | 240–241 |
| 110 | —H | —CH₃ | —H | —H | 215–216 |
| 111 | —H | —H | —CH₃ | —H | 205–206 |
| 112 | —H | —H | —H | —CH₃ | 213–214 |
| 113 | —H | —CH₂—CH₃ | —H | —H | 147–148 |
| 114 | —H | —CH₂—CH₂—CH₃ | —H | —H | 151–152 |
| 115 | —H | —CH(CH₃)₂ | —H | —H | 142–143 |

TABLE I-continued

| Compound No. | R₁ | R₂ | R₃ | R₄ | Melting point °C. |
|---|---|---|---|---|---|
| 116 | —H | —CH(CH₃)—CH₂—CH₃ | —H | —H | 104–105 |
| 117 | —H | —H | —H | —CH(CH₃)CH₂CH | 144–145 |
| 118 | —H | —C(CH₃)₂—CH₂—C(CH₃)₂—CH₃ | —H | —H | 200–201 |
| 119 | —H | —C₁₂H₂₅ | —H | —H | resinous product |
| 120 | —H | —C₆H₁₁ (cyclohexyl) | —H | —H | 233–234 |
| 121 | —H | —(CH₂)₂—COOCH₃ | —H | —H | 150–151 |
| 122 | —H | —(CH₂)₂—COOH | —H | —H | 286–287 |
| 123 | —H | —(CH₂)₂—CN | —H | —H | 243–244 |
| 124 | —H | —CH₂—C₆H₅ | —H | —H | 199–200 |
| 125 | —H | —C(CH₃)₂—C₆H₅ | —H | —H | 194–195 |
| 126 | —H | —COOCH₃ | —H | —H | 294–295 |
| 127 | —H | —COOH | —H | —H | >350 |
| 128 | —H | —COONa | —H | —H | >350 |
| 129 | —H | —COOCH₃ | —H | —O—CH₃ | 273–276 |
| 130 | —H | —H | —COOC₂H₅ | —H | 243–244 |
| 131 | —H | —COO(CH₂)₃CH₃ | —H | —H | 189–190 |
| 132 | —H | —COO(CH₂)₁₇CH₃ | —H | —H | 145–146 |
| 133 | —H | —COOCH₂CH=CH₂ | —H | —H | 200–202 |
| 134 | —H | —COO(CH₂)₃OCH₃ | —H | —H | 185–186 |
| 135 | —H | —COOCH₂—C₆H₅ | H | H | 229–230 |
| 136 | —H | —COO—C₆H₄—C(CH₃)₂—CH₂—C(CH₃)₂—CH₃ | —H | —H | 251–252 |
| 137 | —H | —CONH(CH₂)₇CH₃ | —H | —H | 292–293 |
| 138 | —H | —CONHCH₂—CH₂—OH | —H | —H | >350 |
| 139 | —H | —SO₂—CH₃ | —H | —H | 347–348 |
| 140 | —H | —SO₂—CH₂—CH₃ | —H | —H | 270–271 |
| 141 | —H | —H | —SO₂CH₃ | —H | 344–345 |

The compounds of the formulae (122), (127) and (128) are obtained by saponification of the compounds of the formulae (121) and (126) with sodium hydroxide in ethylene glycol monomethyl ether.

The compounds of the formulae (132), (133), (135), (136) and (138) are obtained by reacting the acid chloride of the compound of the formula (127) with n-octadecanol, allyl alcohol, benzyl alcohol, 4-(1,1'-3,3'-tetramethylbutyl)-phenol or ethanolamine.

The compound of the formula (137) is obtained by reacting the compound of the formula (126) with n-octylamine.

EXAMPLE 10

11.2 g of potassium hydroxide are dissolved in 150 ml of methanol and the clear solution is cooled to 0° C. To this cooled solution is then added dropwise, with stirring and under nitrogen, 10.5 g of diacetyl and 29.6 g of the sulphide of the formula (101) in the course of 30 minutes. The dark brown reaction mixture is then further stirred overnight at room temperature, in the course of which the reaction product of the formula

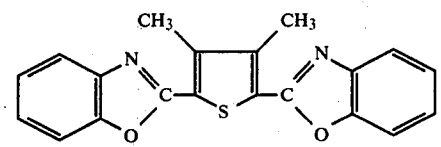
(142)

precipitates in partially crystalline form. The reaction mixture is then acidified with dilute hydrochloric acid, and filtered by suction. The filter cake is washed neutral with water and dried in vacuo, giving 31 g (89% of theory) of a slightly brownish crystalline powder with a melting point of 236°–248° C. Pale yellow crystals with a melting point of 250°–251° C. are obtained after two recrystallisations from chlorobenzene with the aid of activated charcoal and fuller's earth.

The compounds of the formula

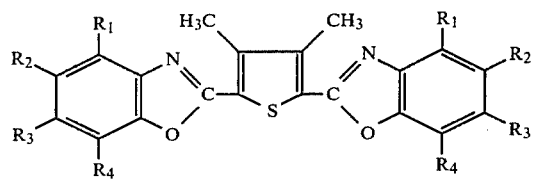

listed in Table II are obtained in analogous manner.

TABLE II

| Compound No. | $R_1$ | $R_2$ | $R_3$ | $R_4$ | Melting point °C. |
|---|---|---|---|---|---|
| 143 | —$CH_3$ | —H | —H | —H | 271–272 |
| 144 | —H | —$CH_3$ | —H | —H | 253–254 |
| 145 | —H | —H | —$CH_3$ | —H | 267–268 |
| 146 | —H | —H | —H | —$CH_3$ | 291–292 |
| 147 | —H | —$CH_2$—$CH_3$ | —H | —H | 195–196 |
| 148 | —H | —$CH_2$—$CH_2$—$CH_3$ | —H | —H | 180–181 |
| 149 | —H | —$C(CH_3)_3$ | —H | —H | 230–232 |
| 150 | —H | —$C_{12}H_{25}$ | —H | —H | resinous product |
| 151 | —H | 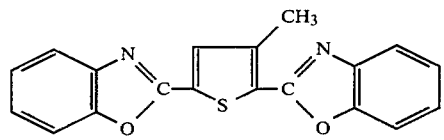 | —H | —H | 237–238 |
| 152 | —H | $CH_2CH_2$—$COOCH_3$ | —H | —H | 156–157 |
| 153 | —H | —$COO(CH_2)_3$—$CH_3$ | —H | —H | 205–206 |
| 154 | —H | —$CH_2$—⟨phenyl⟩ | —H | —H | 216–217 |
| 155 | —H | —$C(CH_3)_2$—⟨phenyl⟩ | —H | —H | 224–225 |

EXAMPLE 11

33.6 g of potassium hydroxide are dissolved in 400 ml of methanol and the clear solution is cooled to 0° C.

66 g of a 40% aqueous methylglyoxal solution and 89 g of the sulphide of the formula (101) are dissolved in 200 ml of dimethyl sulphoxide and this solution is added dropwise, with stirring and under nitrogen, to the above cooled potassium hydroxide-methanol solution in the course of 30 minutes. The reaction mixture is then further stirred for 6 hours at 0° to 5° C. under nitrogen, in the course of which the reaction product of the formula (156)

precipitates in partially crystalline form. The reaction mixture is then acidified with dilute hydrochloric acid and freed from methanol in vacuo. The residue is taken up in methylene chloride, washed neutral with water, dried over sodium sulphate and concentrated to dryness in vacuo, giving 91 g (92% of theory) of a brownish crystalline slurry. Pale yellow crystals with a melting point of 210°–213° C. are obtained after two recrystallisations from chlorobenzene with the aid of activated charcoal and fuller's earth.

EXAMPLE 12

11.2 g of potassium hydroxide are dissolved in 200 ml of methanol and the clear solution is cooled to 0° C.

13 g of pentane-2,3-dione and 29.6 g of the sulphide of the formula (101) are dissolved in 100 ml of dimethyl sulphoxide and this solution is added dropwise, with stirring and nitrogen, to the above cooled methanolic potassium hydroxide solution in the course of 30 minutes. The reaction mixture is further stirred for 4 hours at 0° C. to 5° C. and subsequently for 16 hours at room temperature under nitrogen. The dark brown reaction mixture is then cooled to 0° C. acidified with dilute hydrochloric acid and filtered by suction. The filter cake is washed neutral firstly with alcohol and then with water and dried in vacuo, giving 7 g (20% of theory) of the compound of the formula

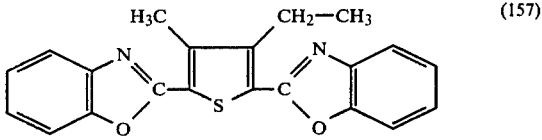

(157)

in the form of a pale yellow crystalline powder with a melting point of 209°–211° C. The product melts at 213°–214° C. after two recrystallisations from chlorobenzene with the aid of activated charcoal.

EXAMPLE 13

The procedure described in Example 12 is repeated, using 13 g of cyclohexane-1,2-dione instead of pentane-2,3-dione. Yield: 31 g (83.3% of theory) of the compound of the formula

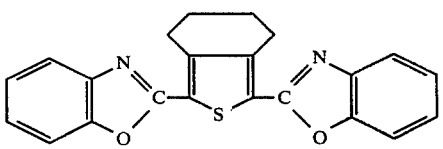

(158)

in the form of a yelloy crystalline powder with a melting point of 273°–282° C. The product melts at 288°–290° C. after two recrystallisations from chlorobenzene with the aid of activated charcoal.

What is claimed is:

1. A process for the manufacture of 2,5-bis-(benzoxazolyl)-thiophene compounds of the formula

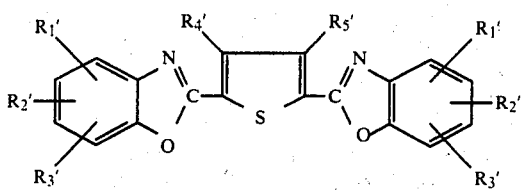

wherein
R$_1'$ represents hydrogen, halogen, alkyl of 1 to 12 carbon atoms, haloalkyl, hydroxyalkyl, cyanoalkyl or phenylalkyl, each containing 1 to 4 carbon atoms in the alkyl moiety, alkyl of 1 to 4 carbon atoms which is substituted by a group of the formula —COOY or —CONY$_1$Y$_2$ in which Y represents hydrogen, an alkali metal, alkaline earth metal or ammonium salt, alkyl of 1 to 18 carbon atoms, alkenyl of 2 to 4 carbon atoms, hydroxyalkyl, cyanoalkyl or phenylalkyl, each containing 1 to 4 carbon atoms in the alkyl moiety, alkoxyalkyl of altogether 2 to 8 carbon atoms, phenyl or phenyl which is substituted by alkyl of 1 to 12 carbon atoms, and each of Y$_1$ and Y$_2$ independently represents hydrogen, alkyl of 1 to 8 carbon atoms, hydroxyalkyl, cyanoalkyl or phenylalkyl each containing 1 to 4 carbon atoms in the alkyl moiety; alkenyl of 3 or 4 carbon atoms, cyclohexyl, alkoxy of 1 to 4 carbon atoms, phenyl, phenoxy, cyano, alkylsulphonyl of 1 to 4 carbon atoms, the sulpho group or an alkali metal salt thereof, or the group of the formula —COOY or —CONY$_1$Y$_2$ in which Y, Y$_1$ and Y$_2$ are as defined above,
R$_2'$ represents hydrogen, alkyl of 1 to 4 carbon atoms or chlorine,
R$_3'$ represents hydrogen or methyl, and each of
R$_4'$ and R$_5'$ independently represents hydrogen, alkyl of 1 to 4 carbon atoms, or together they represent the trimethylene or tetramethylene radical
which process comprises reacting in an inert solvent at a temperature of −5° C. to 100° C. in the presence of a base or an acid a sulfide of the formula

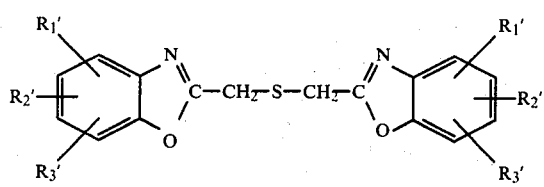

wherein R$_1'$, R$_2'$ and R$_3'$ are as defined above, with a compound of the formula

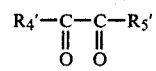

wherein R$_4'$ and R$_5'$ are as defined above or an acetal, ketal, imine, oxime, hydrozone, sulfate, bisulfite or hydrate functional derivative thereof.

2. A process according to claim 1 for the manufacture of 2,5-bis-(benzoxazolyl)-thiophene compounds of the formula

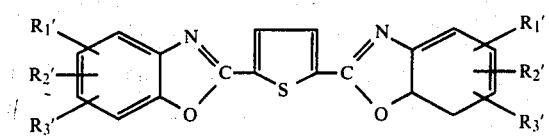

wherein
R$_1'$ represents hydrogen halogen, alkyl of 1 to 12 carbon atoms, haloalkyl, hydroxyalkyl, cyanoalkyl or phenylalkyl, each containing 1 to 4 carbon atoms which is substituted by a group of the formula —COOY or —CONY$_1$Y$_2$, in which Y represents hydrogen, a salt forming cation, alkyl of 1 to 18 carbon atoms, alkynyl of 2 to 4 carbon atoms, hydroxyalkyl, cyanoalkyl or phenylalkyl, each containing 1 to 4 carbon atoms in the alkyl moiety, alkoxyalkyl of altogether 2 to 8 carbon atoms, phenyl or phenyl which is substituted by alkyl of 1 to 12 carbon atoms, and each of y$_1$ and Y$_2$ independently represents hydrogen, alkyl of 1 to 8 carbon atoms, hydroxyalkyl, cyanoalkyl or phenylalkyl, each containing 1 to 4 carbon atoms in the alkyl moiety; alkenyl of 3 or 4 carbon atoms, cyclohexyl, alkoxy of 1 to 4 carbon atoms, phenyl, phenoxy, cyano, alkylsulphonyl of 1 to 4 carbon atoms, the sulpho group or an alkali metal salt thereof, or a group of the formula —COOY or —CONY$_1$Y$_2$ in which Y, Y$_1$ and Y$_2$ are as defined above,
R$_2'$ represents hydrogen, alkyl of 1 or 4 carbon atoms, alkoxy of 1 to 4 carbon atoms or chloride and
R$_3'$ represents hydrogen or methyl,
which process comprises reacting a sulphide of the formula

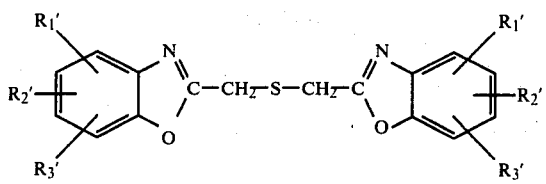

wherein R$_1'$, R$_2'$ and R$_3'$ are as defined above, with glyoxal, trimeric glyoxal hydrate, polymeric glyoxal, glyoxal bisulfite, glyoxal sulphate or with an acetal, hemiacetal, mono- or bisaldimine, mono- or bisaldoxine or hydrazone of glyoxal.

3. A process according to claim 1 for the manufacture of 2,5-bis-(benzoxazolyl)-thiophene compounds of the formula

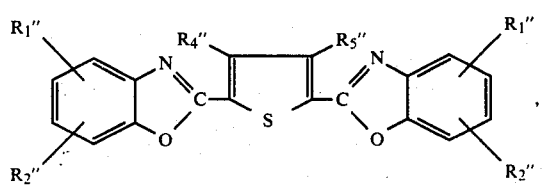

wherein
R₁" represents hydrogen, chlorine, alkyl or 1 to 12 carbon atoms, cyanoalkyl or phenylalkyl, each containing 1 to 4 carbon atoms in the alkyl moiety, carboxyalkyl of 2 to 5 carbon atoms, carbalkoxyalkyl of 3 to 9 carbon atoms, phenyl, cyclohexyl, alkoxy of 1 to 4 carbon atoms, alkylsulphonyl of 1 to 4 carbon atoms, a group of the formula —COOY', in which Y' represents hydrogen, alkyl of 1 to 18 carbon atoms, alkoxyalkyl of altogether 2 to 6 carbon atoms, phenylalkyl containing 1 to 4 carbon atoms in the alkyl moiety, alkenyl containing 3 or 4 carbon atoms or an alkali metal or ammonium ion, or a group of the formula —CONY₁'Y₂' in which Y₁' represents hydrogen, alkyl of 1 to 8 carbon atoms or hydroxyalkyl of 1 to 4 carbon atoms and Y₂' represents a hydrogen or alkyl of 1 to 4 carbon atoms, R₂" represents hydrogen, alkyl of 1 to 4 carbon atoms or alkoxy of 1 to 4 carbon atoms, and each of
R₄" and R₅" represents hydrogen, alkyl of 1 to 4 carbon atoms or together they represent the tetramethylene radical, which process comprises reacting a sulphide of the formula

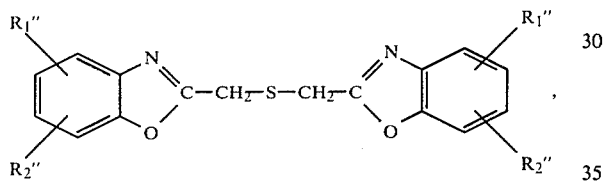

wherein R"₁ and R"₂ have the given meanings, with a compound of the formula

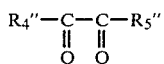

wherein R"₄ and R"₅ are as defined above, or with said functional derivative thereof.

4. A process according to claim 1 for the manufacture of 2,5-bis-(benzoxazolyl)-thiophene compounds of the formula

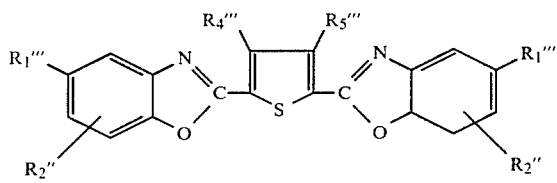

wherein R₁" represents hydrogen, alkyl of 1 to 12 carbon atoms, cyclohexyl, carboxalkyl of 2 to 5 carbon atoms, carbalkoxyalkyl of 3 to 9 carbon atoms, phenylalkyl containing 1 to 4 carbon atoms in the alkyl moiety, phenyl, carboxyl, carbalkoxy of 2 to 5 carbon atoms or alkylsulphonyl of 1 to 4 carbon atoms, R₄'" and R₅'" independently represent hydrogen or alkyl of 1 to 4 carbon atoms, and R₂" is hydrogen, alkyl of 1 to 4 carbon atoms or alkoxy of 1 to 4 carbon atoms, which process comprises reacting a sulphide of the formula

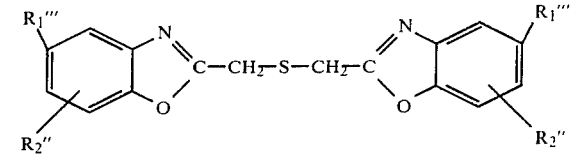

wherein R₁'" and R₂'" have the given meanings, with an α,β-dicarbonyl compound of the formula

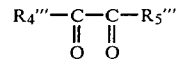

wherein R₄'" and R₅'" have the given meanings, or with said functional derivative thereof.

5. A process according to claim 3 for the manufacture of 2,5-bis-(benzoxazolyl)-thiophene compounds of the formula

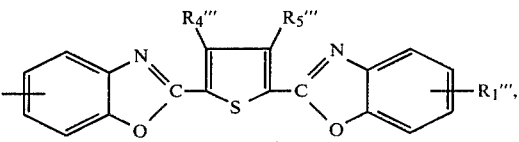

wherein
R₁'" represents hydrogen, alkyl of 1 to 12 carbon atoms, cyclohexyl, carboxyalkyl of 2 to 5 carbon atoms, carbalkoxyalkyl of 3 to 9 carbon atoms, phenylalkyl containing 1 to 4 carbon atoms in the alkyl moiety, phenyl, carboxyl, carbalkoxy of 2 to 5 carbon atoms or alkylsulphonyl of 1 to 4 carbon atoms, and each of
R₄'" and R₅'" independently represents hydrogen or alkyl of 1 to 4 carbon atoms,
which process comprises reacting a mulphide of the formula

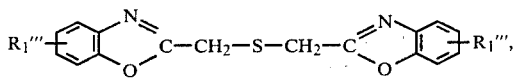

wherein R'"₁ has the given meaning, with an α,β-dicarbonyl compound of the formula

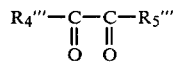

wherein R'"₄ and R'"₆ have the given meanings, or with said functional derivative thereof.

6. A process according to claim 1 for the manufacture of 2,5-bis-(benzoxazolyl)-thiophene compounds of the formula

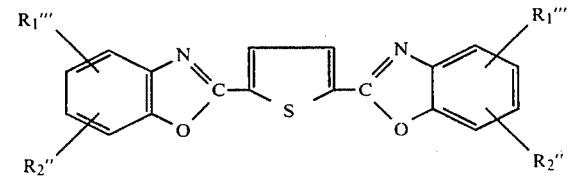

wherein R₁'" represents hydrogen, alkyl of 1 to 12 carbon atoms, cyclohexyl, carboxyalkyl of 2 to 5 carbon atoms, carbalkoxyalkyl of 3 to 9 carbon atoms, phenylalkyl containing 1 to 4 carbon atoms in the alkyl moiety, phenyl, carboxyl, carbalkoxy of 2 to 5 carbon atoms or alkylsulphonyl of 1 to 4 carbon atoms, and $R_2$ is hydrogen, alkyl of 1 to 4 carbon atoms or alkoxy of 1 to 4 carbon atoms, which process comprises reacting a sulphide of the formula

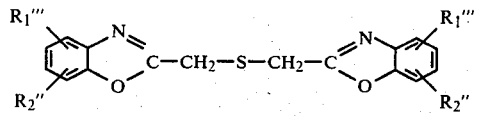

wherein $R_1'''$ and $R_2'''$ have the meanings, with glyoxal, trimeric or polymeric glyoxal, glyoxal bisulphite or glyoxal bisaldimes.

7. A process according to claim 1 wherein the reaction is carried out at a temperature between 0° C. to 50° C.

8. A process according to claim 6 for the manufacture of 2,5-bis-(benzoxazolyl)-thiophene compounds of the formula

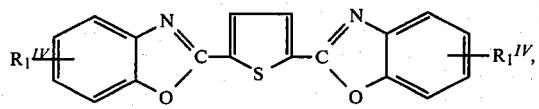

wherein $R_1^{IV}$ represents hydrogen, alkyl of 1 to 4 carbon atoms, chlorine, alkylsulphenyl of 1 to 4 carbon atoms, carboxyl, carbalkoxy of 2 to 5 carbon atoms, benzyl or α,α-dimethylbenzyl, which process comprises reacting a sulphide of the formula

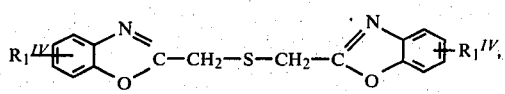

wherein $R_1^{IV}$ has the given meaning, with glyoxal.

9. A process according to claim 8 for the manufacture of 2,5-bis-(benzoxazolyl)-thiophene compounds of the formula

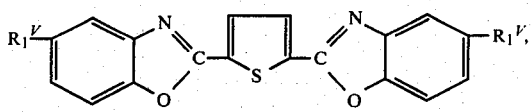

wherein $R_1^V$ represents hydrogen, alkyl of 1 to 4 carbon atoms, benzyl, α,α-dimethylbenzyl or chlorine, which process comprises reacting a mulphide of the formula

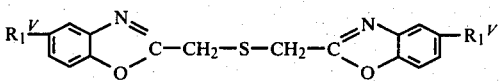

wherein $R_1^V$ has the given meaning, with glyoxal.

10. A process according to claim 1 wherein the base is an alcoholate or hydroxide of an alkali metal.

* * * * *